US011676440B2

(12) United States Patent
Di Genova

(10) Patent No.: US 11,676,440 B2
(45) Date of Patent: *Jun. 13, 2023

(54) SYSTEMS AND METHODS FOR PHARMACEUTICAL DISPENSING

(71) Applicant: Express Scripts Strategic Development, Inc., St. Louis, MO (US)

(72) Inventor: Gabriel Di Genova, Wildwood, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/827,672

(22) Filed: May 28, 2022

(65) Prior Publication Data

US 2022/0292909 A1 Sep. 15, 2022

Related U.S. Application Data

(63) Continuation of application No. 17/013,904, filed on Sep. 8, 2020, now Pat. No. 11,348,398.

(51) Int. Cl.
| | | |
|---|---|---|
| *G16H 20/13* | (2018.01) | |
| *G07F 13/02* | (2006.01) | |
| *A61J 7/02* | (2006.01) | |
| *G07F 17/00* | (2006.01) | |

(52) U.S. Cl.
CPC .............. *G07F 13/025* (2013.01); *A61J 7/02* (2013.01); *G07F 17/0092* (2013.01); *G16H 20/13* (2018.01)

(58) Field of Classification Search
CPC ... G07F 17/0092; G07F 13/025; B65B 5/103; B65B 57/20; A61J 7/02; B16H 20/13
See application file for complete search history.

(56) References Cited

U.S. PATENT DOCUMENTS

| | | |
|---|---|---|
| 2,134,180 A | 10/1938 | Felber |
| 5,133,478 A | 7/1992 | Gordon |
| 5,348,061 A | 9/1994 | Riley |
| 6,499,270 B2 | 12/2002 | Peroni |
| 6,681,550 B1 * | 1/2004 | Aylward ................. B65B 5/103 53/244 |
| 6,899,148 B1 | 5/2005 | Geltser |
| 6,918,509 B2 | 7/2005 | Baker |
| 7,255,247 B2 | 8/2007 | Aylward |
| 7,631,670 B2 | 12/2009 | Geltser |

(Continued)

*Primary Examiner* — Timothy R Waggoner
(74) *Attorney, Agent, or Firm* — Stinson LLP

(57) ABSTRACT

A pharmaceutical dispenser for dispensing a quantity of pharmaceuticals into a container includes a pharmaceutical counter to count and release the quantity of pharmaceuticals. A pharmaceutical outlet delivers the quantity of pharmaceuticals to the container. A pharmaceutical gate receives the quantity of pharmaceuticals from the pharmaceutical counter. The pharmaceutical gate includes a receiver sized and shaped to define a pharmaceutical receiving space to hold the quantity of pharmaceuticals. The receiver moves between a receiving position and a dispensing position. In the receiving position, the receiver receives the quantity of pharmaceuticals in the pharmaceutical receiving space from the pharmaceutical counter. In the dispensing position, the receiver dispenses the quantity of pharmaceuticals toward the pharmaceutical outlet.

20 Claims, 11 Drawing Sheets

(56) References Cited

U.S. PATENT DOCUMENTS

| | | | |
|---|---|---|---|
| 7,931,670 B2 * | 4/2011 | Fiehler | A61B 17/0057 |
| | | | 606/232 |
| 8,386,073 B2 | 2/2013 | Kim | |
| 8,511,478 B2 | 8/2013 | Terzini | |
| 8,862,266 B2 | 10/2014 | Van Ooyen | |
| 9,697,335 B2 | 7/2017 | Joplin | |
| 9,833,356 B2 | 12/2017 | Wochele | |
| 10,189,698 B2 | 1/2019 | Proper | |
| 10,303,854 B2 | 5/2019 | Joplin | |
| 11,348,398 B1 * | 5/2022 | Di Genova | A61J 7/02 |
| 2003/0006242 A1 | 1/2003 | McKinney, Jr. | |
| 2005/0045652 A1 * | 3/2005 | Maser | B01F 21/20 |
| | | | 221/265 |
| 2005/0113968 A1 | 5/2005 | Williams | |
| 2006/0243738 A1 | 11/2006 | Yuyama | |
| 2006/0272638 A1 | 12/2006 | Brickl | |
| 2010/0185458 A1 | 7/2010 | Newcomb | |
| 2014/0244033 A1 | 8/2014 | Ucer | |
| 2015/0166247 A1 | 6/2015 | Ashbaugh | |
| 2016/0355322 A1 | 12/2016 | Burton, Jr. | |

\* cited by examiner

SYSTEMS AND METHODS FOR PHARMACEUTICAL DISPENSING

CROSS REFERENCE TO RELATED APPLICATIONS

This application is a continuation of U.S. application Ser. No. 17/013,904, which was filed Sep. 8, 2020. The entire disclosure of said application is incorporated herein by reference.

FIELD

The present disclosure generally relates to pharmaceutical fulfillment systems, and more particularly to pharmaceutical dispensing systems for dispensing pharmaceuticals.

BACKGROUND

Pharmaceutical fulfillment systems process and fill a large number of prescriptions and prescription orders with pharmaceuticals. Such fulfillment systems may include automated dispensing systems that supply a specified quantity of pharmaceuticals to prescription containers.

BRIEF SUMMARY

In one aspect, a pharmaceutical dispenser for dispensing a quantity of pharmaceuticals into a container comprises a pharmaceutical counter configured to count and release the quantity of pharmaceuticals. A pharmaceutical outlet delivers the quantity of pharmaceuticals to the container. A pharmaceutical gate is configured to receive the quantity of pharmaceuticals from the pharmaceutical counter. The pharmaceutical gate includes a receiver sized and shaped to define a pharmaceutical receiving space to hold the quantity of pharmaceuticals. The receiver is movable between a receiving position and a dispensing position. In the receiving position, the receiver is configured to receive the quantity of pharmaceuticals in the pharmaceutical receiving space from the pharmaceutical counter. In the dispensing position, the receiver is configured to dispense the quantity of pharmaceuticals toward the pharmaceutical outlet.

In another aspect, a method for dispensing a quantity of pharmaceuticals into a container comprises counting the quantity of pharmaceuticals with a pharmaceutical counter, collecting the quantity of pharmaceuticals from the pharmaceutical counter with a pharmaceutical gate, the pharmaceutical gate including a receiver sized and shaped to define a pharmaceutical receiving space to hold the quantity of pharmaceuticals, and dispensing the quantity of pharmaceuticals from the pharmaceutical gate toward the container by moving the receiver toward a dispensing position to permit the quantity of pharmaceuticals to flow out of the receiver.

In another aspect, a pharmaceutical gate for dispensing pharmaceuticals into a container comprises a housing having an inlet opening configured to receive the pharmaceuticals, an outlet opening configured to outlet the pharmaceuticals toward the container, and a pharmaceutical passage extending between and interconnecting the inlet opening and the outlet opening. A receiver is disposed in the pharmaceutical passage. The receiver is sized and shaped to define a pharmaceutical receiving space to hold the pharmaceuticals. The receiver is turnable between a receiving position and a dispensing position. In the receiving position, the receiver is configured to receive the pharmaceuticals in the pharmaceutical receiving space as the pharmaceuticals flow through the inlet opening and to block the pharmaceuticals from reaching the outlet opening. In the dispensing position, the receiver is configured to dispense the pharmaceuticals through the outlet opening. A prime mover is operatively coupled to the receiver. The prime mover is configured to turn the receiver between the receiving position and the dispensing position. A gate controller is communicatively coupled to the prime mover and configured to operate the prime mover to turn the receiver toward the dispensing position when the container is in a position to receive the pharmaceuticals.

Other objects and features of the present disclosure will be in part apparent and in part pointed out herein.

BRIEF DESCRIPTION OF THE DRAWINGS

Corresponding reference characters indicate corresponding parts throughout the drawings.

DETAILED DESCRIPTION

Figure 1:
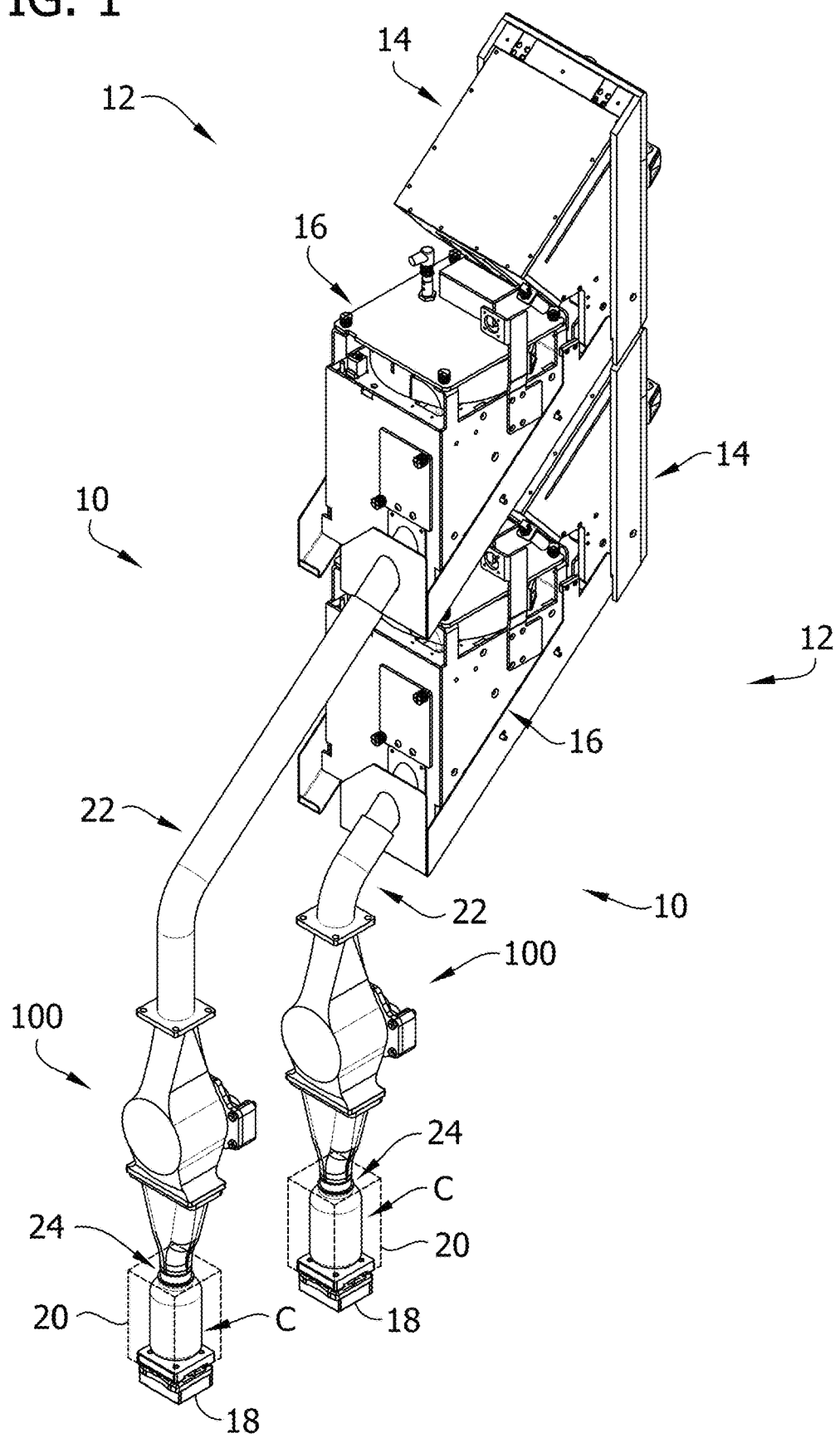
FIG. 1 is a perspective of two pharmaceutical dispensers arranged in an array.
Figure 2:
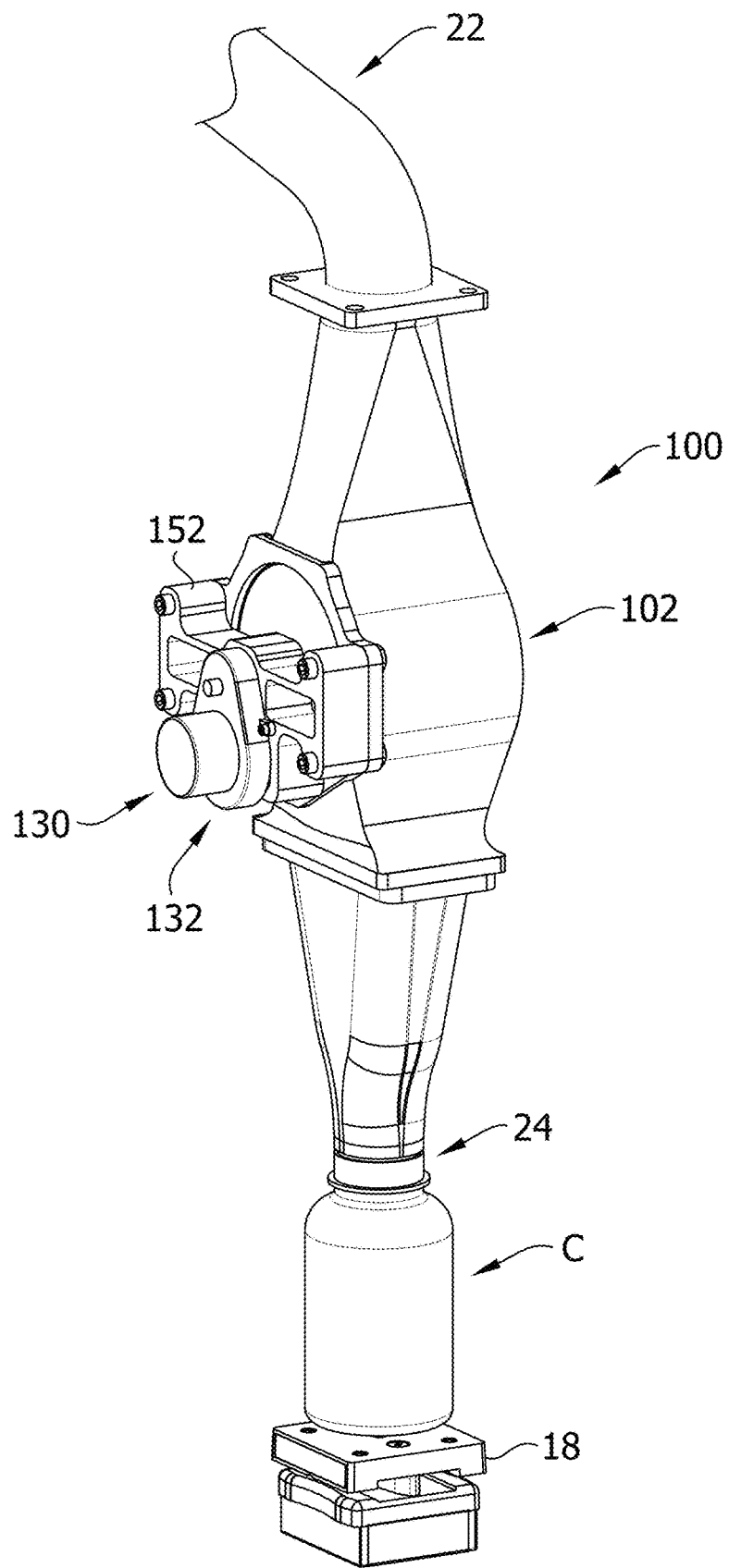
FIG. 2 is an enlarged perspective of one of the pharmaceutical dispensers.
Figure 3:
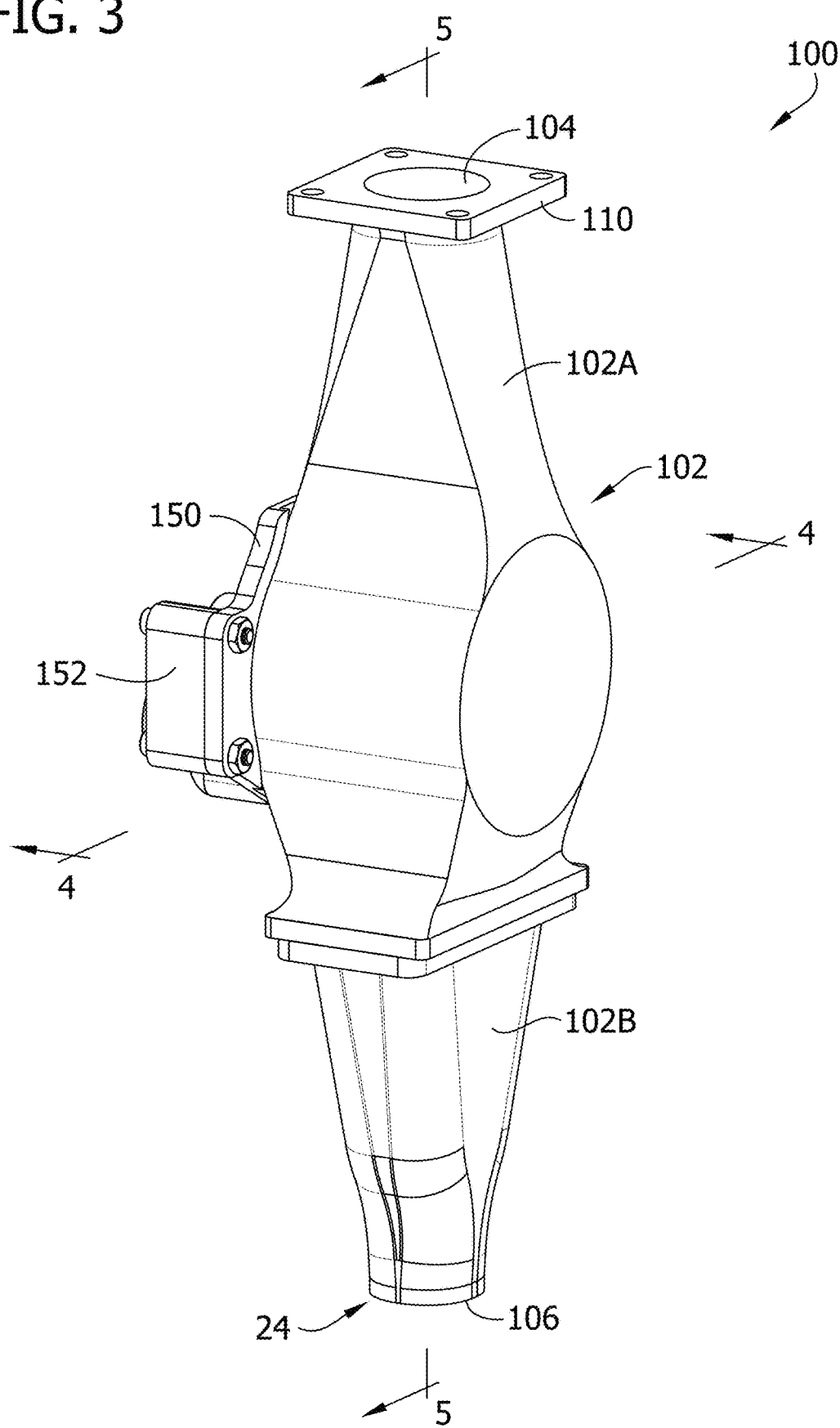
FIG. 3 is a perspective of a pharmaceutical gate of the pharmaceutical dispenser according to one embodiment of the present disclosure.

Referring to FIGS. 1 and 2, a pharmaceutical or pill gate according to one embodiment of the present disclosure is generally indicated at 100. The pharmaceutical gate 100 is part of a pharmaceutical dispenser 10 that dispenses pharmaceuticals P (e.g., prescription drugs) (FIG. 4) to a container C. The pharmaceutical dispenser 10 is used in a pharmaceutical order processing system 2 (FIG. 8), such as a high volume pharmaceutical order processing system, to fulfill a prescription order received by the pharmaceutical order processing system. An example of the pharmaceutical order processing system is described in U.S. Pat. No. 9,697,335, which is hereby incorporated by reference. In an example embodiment, the pharmaceutical gate 100 can be placed in-line with the buffer tube in U.S. Pat. No. 9,697,335. The prescription order may include one or more pharmaceuticals P. The pharmaceuticals P dispensed by the pharmaceutical dispenser 10 may be in the form of pills, capsules, geltabs, tablets, or the like.

The pharmaceutical dispenser 10 includes the pharmaceutical gate 100, a pharmaceutical or pill counter 12, a pharmaceutical outlet 24, and a container station 20. The pharmaceutical dispenser 10 may also include pharmaceutical plumbing 22 (e.g., pipes, tubes, chutes, ducts, fittings, etc.) connecting these components and stations together to guide (e.g., move) the pharmaceuticals P therebetween (e.g., from the pharmaceutical counter 12 to the container C). The pharmaceutical counter 12 is configured to count and release the specified quantity (e.g., exact counts) of pharmaceuticals P to fulfill a prescription order. The pharmaceutical counter 12 includes a hopper 14 configured to store a plurality of pharmaceuticals P and a counting mechanism 16 configured to count and release the exact number of pharmaceuticals needed to fill a prescription order. The pharmaceutical outlet 24 delivers (e.g., outputs, guides, directs) the pharmaceuticals P to the container C.

The container station 20 is the area or location where the container C is positioned to collect the pharmaceuticals P dispensed by the pharmaceutical dispenser 10 through the pharmaceutical outlet 24. Each container C is supported by a platform 18, which may move the container C into the container station 20 to collect the dispensed pharmaceuticals P and moves the container out of the container station once the container is filled with the dispensed pharmaceuticals. In the illustrated embodiment, two pharmaceutical dispensers 10 are arranged in an array to form an automated dispensing system. It is understood the array of an automated dispensing system can include many (e.g., 10, 20, 30, 40, 50 or more) pharmaceutical dispensers 10. In such a configuration, generally each pharmaceutical dispenser 10 dispenses one type of pharmaceutical. Further details on pharmaceutical order processing systems, automated dispensing systems, pharmaceutical dispensers and components thereof may be found in U.S. Pat. No. 10,303,854, the entirety of which is hereby incorporated by reference. It is appreciated that the systems and components described herein can be used in other contexts without departing from the scope of the present disclosure.

The pharmaceutical gate 100 acts as a pharmaceutical buffer between the pharmaceutical counter 12 and the container C at the container station 20. The pharmaceutical gate 100 is configured to receive the pharmaceuticals P (e.g., quantity of pharmaceuticals, such as a number of pills) from the pharmaceutical counter 12. The pharmaceutical gate 100 then holds (e.g., retains) the pharmaceuticals P until the time when pharmaceuticals are ready to be dispensed (e.g., released) to the container C at the container station 20 through the pharmaceutical outlet 24. For example, the pharmaceutical gate 100 releases the pharmaceuticals P when a container C is positioned at the container station 20. The pharmaceutical gate 100 can receive pharmaceuticals before, while, or after the container C is moved into position to receive the pharmaceuticals from the gate. The pharmaceuticals P flow out of the pharmaceutical gate 100 (and through any pharmaceutical plumbing 22), through the pharmaceutical outlet 24 and into the container C. The pharmaceuticals P flow under the influence of gravity from the pharmaceutical counter 12 to the pharmaceutical gate 100 and then from the pharmaceutical gate to the pharmaceutical outlet 24.

Referring to FIGS. 3-7, the pharmaceutical gate 100 includes a housing 102 having an inlet opening 104 and an outlet opening 106. The inlet opening 104 is configured to receive the pharmaceuticals P from the pharmaceutical counter 12. The inlet opening 104 is communicatively (e.g., fluidly) coupled to the pharmaceutical counter 12 via the pharmaceutical plumbing 22 to receive the pharmaceuticals P from the counter as the counter counts and releases the specific quantity of pharmaceuticals to fill a prescription order. The housing 102 includes a mounting flange 110 adjacent the inlet opening 104 to connect the housing to the pharmaceutical plumbing 22. The outlet opening 106 is configured to outlet the pharmaceuticals P toward the container station 20 and the container C disposed therein. In the illustrated embodiment, the outlet opening 106 of the housing 102 defines the pharmaceutical outlet 24. The pharmaceutical gate 100 is arranged such that the pharmaceuticals P flow directly out of the outlet opening 106 and into the container C at the container station 20. The size and shape of the outlet opening 106 generally corresponds to the opening of the container C to direct the pharmaceuticals P into the container. In other embodiments, the outlet opening 106 may be spaced apart from the pharmaceutical outlet 24 such that the pharmaceutical dispenser 10 may include additional pharmaceutical plumbing 22 (not shown) extending from the outlet opening to the pharmaceutical outlet to guide the pharmaceuticals P to the container C. It is understood the pharmaceutical gate 100 can be located at generally any position along the pharmaceutical flow path extending between the pharmaceutical counter 12 and the pharmaceutical outlet 24. The housing 102 also includes a pharmaceutical passage 108 extending between the inlet opening 104 and the outlet opening 106. The pharmaceutical passage 108 communicatively couples (e.g., interconnects) the inlet and outlet openings 104, 106. The pharmaceuticals P generally flow from the inlet opening 104 to the outlet opening 106 through the pharmaceutical passage 108. The pharmaceutical passage 108 is defined by one or more walls of the housing 102. The one or more walls have smooth interiors to facilitate the follow of the pharmaceuticals P through the pharmaceutical passage 108. The housing 102 includes one or more walls (e.g., side walls) defining a generally cylindrical upper portion of the pharmaceutical passage 108 extend from the inlet opening 104, a plurality of side walls defining an intermediate portion of the pharmaceutical passage 108 (which houses the receiver 114, described below), and a plurality of side walls, that are generally rectangular arranged and tapered inward toward the outlet opening 106, defining a lower portion of the pharmaceutical passage.

The housing 102 may be an integral, one-piece component or may be formed from multiple pieces coupled together. In the illustrated embodiment, the housing 102 includes an upper housing portion 102A and a lower housing portion 102B coupled together. The upper and lower housing portions 102A, 102B include interface openings 112A, 112B at the interface of the upper and lower housing portions to communicatively couple the housing portions together. Desirably, the interface opening 112B of the lower housing portion 102B is larger than the interface opening 112A of the upper housing portion 102A to prevent the formation of any ledges or shoulders in the pharmaceutical passage 108 at the interface that may restrict, capture or trap pharmaceuticals P flowing through the passage. In other words, the peripheral edges of the interface opening 112B of the lower housing portion 102B are disposed outward of the peripheral edges of the interface opening 112A of the upper housing portion 102A when the housing portions are coupled together. In the illustrated embodiment, the peripheral edges of the interface opening 112B of the lower housing portion 102B are also rounded or filleted to further reduce the possibility of restricting, capturing or trapping any of the pharmaceuticals P. The upper and lower housing portions 102A, 102B include smooth inner walls that the define the pharmaceutical passage 108 through which the pharmaceuticals P move, to facilitate the flow of the pharmaceuticals.

Figure 4:
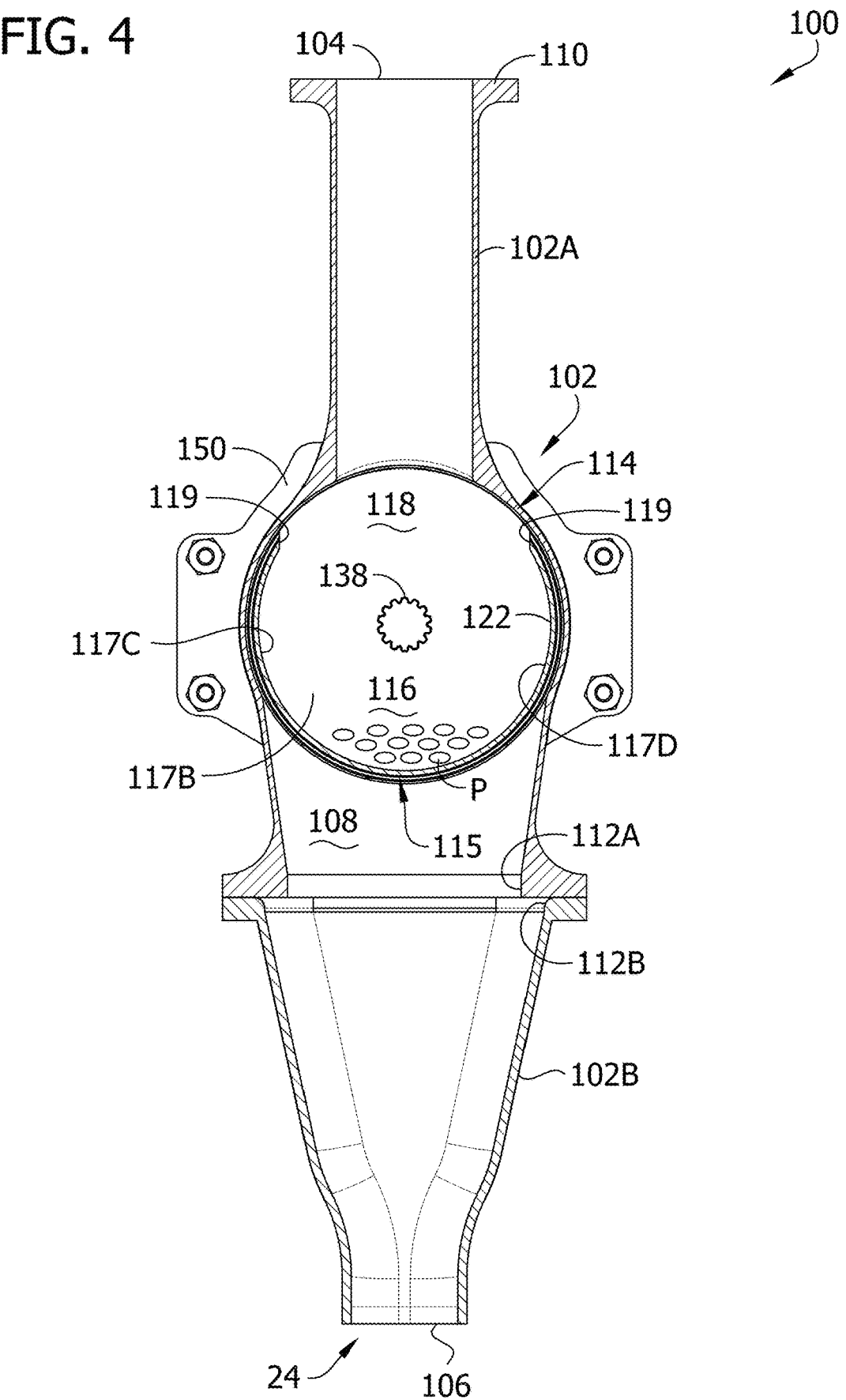
FIG. 4 is a cross section of the pharmaceutical gate taken through line 4-4 of FIG. 3 with a receiver in a receiving position.
Figure 5:
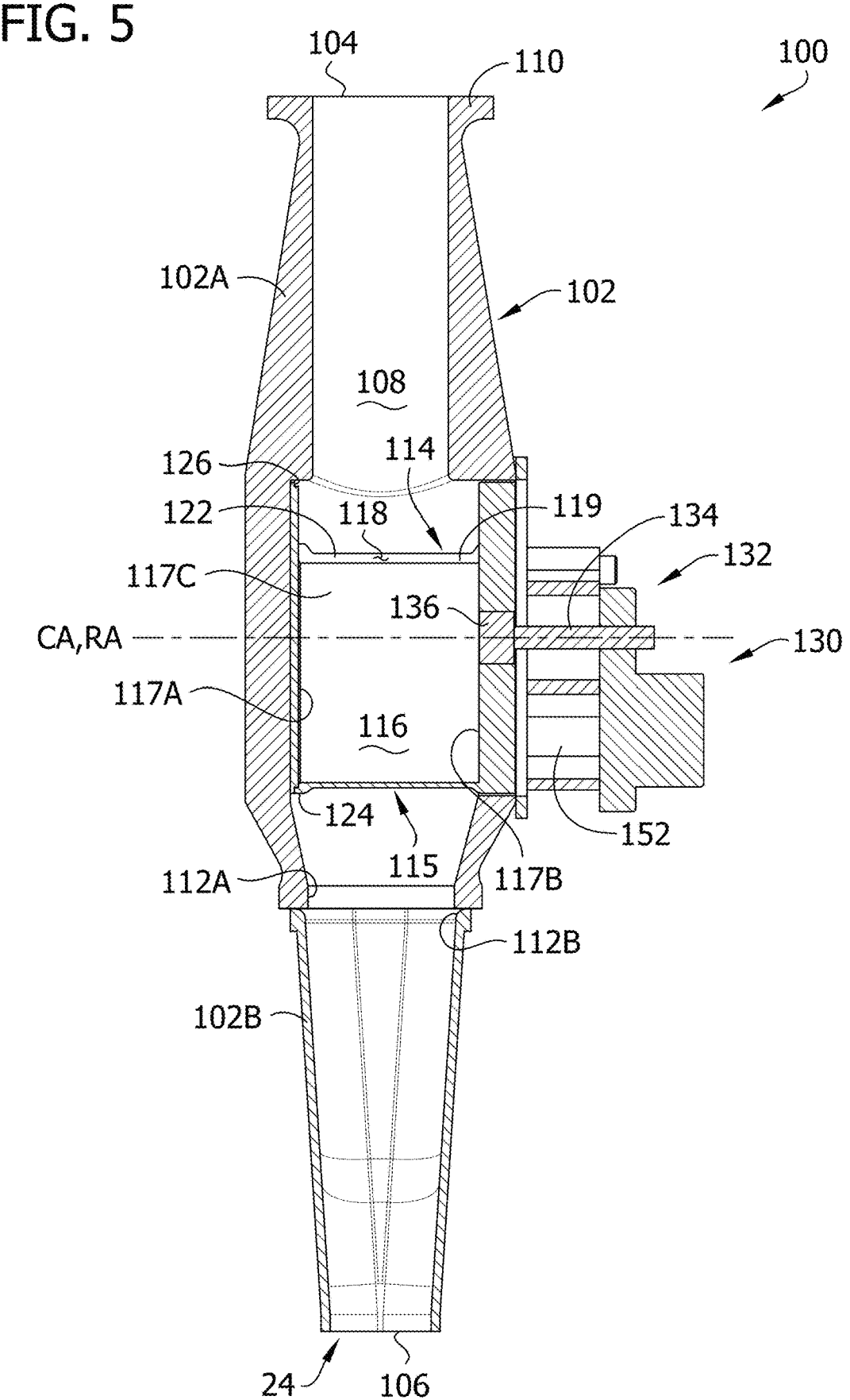
FIG. 5 is a cross section of the pharmaceutical gate taken through line 5-5 of FIG. 3.
Figure 6:
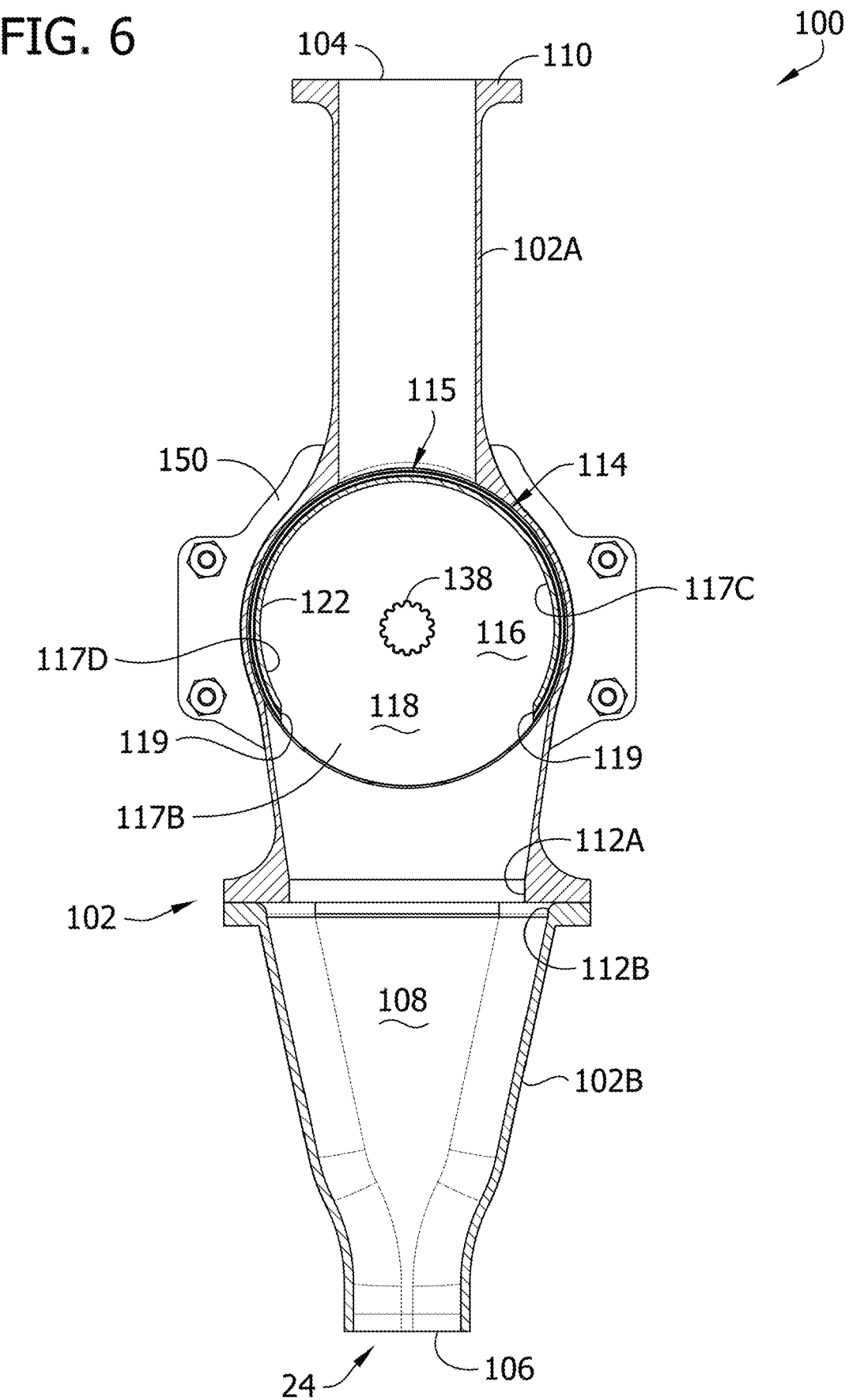
FIG. 6 is a cross section of the pharmaceutical gate taken through line 4-4 of FIG. 3 with the receiver in a dispensing position.
Figure 7:
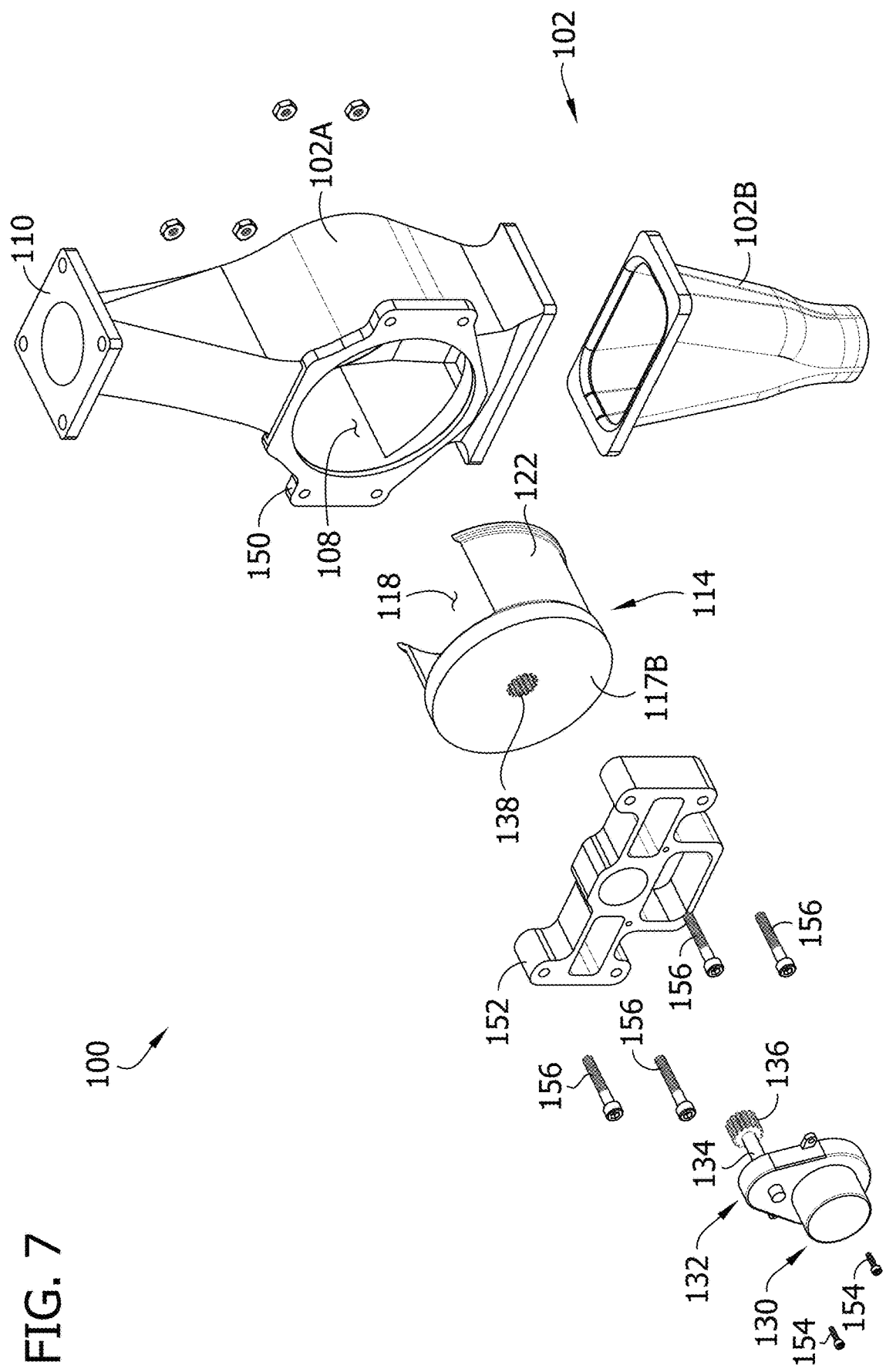
FIG. 7 is an exploded view of the pharmaceutical gate.

Referring to FIGS. 4-7, the pharmaceutical gate 100 includes a receiver 114 configured (e.g., sized and shaped) to receive and hold the pharmaceuticals P from the pharmaceutical counter 12 and then dispense the pharmaceuticals toward the pharmaceutical outlet 24 when there is a container C at the container station 20. The receiver 114 is disposed in the pharmaceutical passage 108. As shown in FIGS. 4-6, the receiver 114 substantially fills a portion (e.g., cross section) of the pharmaceutical passage 108 so that any pharmaceuticals P flowing through the pharmaceutical passage flow into the receiver. The receiver 114 includes (e.g., defines) a pharmaceutical receiving volume or space 116 (broadly, at least one pharmaceutical receiving space) sized and shaped to hold the pharmaceuticals P. Desirably, the pharmaceutical receiving space 116 is sized and shaped to hold a variety of different quantities (e.g., 30, 60, 120) and sizes (e.g., pill sizes) of pharmaceuticals P. As will become apparent, the receiver 114 rotates to dispense the pharmaceuticals P it holds.

The receiver 114 includes a mouth 118 in communication with the receiving space 116. The mouth 118 is sized and shaped to enable the pharmaceuticals P to enter and leave the pharmaceutical receiving space 116. As can be seen in FIG. 4, the mouth 118 has a width less than the largest width of the pharmaceutical receiving space 116. Desirably, the mouth 118 of the pharmaceutical receiving space 116 is larger than the inlet opening 104 and, more desirably, the portion (e.g., upper portion) of the pharmaceutical passage 108 immediately upstream of the mouth when the receiver is in the receiving position. For example, the width of the mouth 118 is desirably the same as or slightly larger than the lower open end of the upper portion of the pharmaceutical passage 108. This way the pharmaceuticals P flow through the inlet opening 104 and into the pharmaceutical receiving space 116, without getting caught or trapped by any part of the pharmaceutical gate 100. In the illustrated embodiment, the portion of the pharmaceutical passage 108 extending from the inlet opening 104 to the receiver 114 is the same size as the inlet opening 104. The pharmaceutical passage 108 then increases in size in order to accommodate the receiver 114.

The receiver 114 includes a base (e.g., a base portion), generally indicated at 115, opposite the mouth 118. The base 115 partially (broadly, at least partially) defines the pharmaceutical receiving space 116. In particular, the base 115 generally defines the bottom of the pharmaceutical receiving space 116. The pharmaceutical receiving space 116 is disposed between the mouth 118 and the base 115. The receiver 114 includes at least one side wall extending upward from the base 115 (when the receiver is in the receiving position). The base 115 and the at least one side wall partially (broadly, at least partially) defining the pharmaceutical receiving space 116. In the exemplary embodiment, the receiver 114 includes opposite front and rear side wall 117A, 117B and opposite left and right side walls 117C, 117D. Together, the base 115 and side walls 117A-D define the pharmaceutical receiving space. Likewise, the side walls 117A-D define the mouth 118. Desirably, the interior surfaces of the left and right side walls 117C, 117D are arcuate or curved (e.g., concave), to help control the movement of the pharmaceuticals P out of the receiver 114. The receiver 114 includes at least one pouring lip 119 over which the pharmaceuticals P are pourable from the receiver. In the exemplary embodiment, the receiver 114 includes two pouring lips 119 defined by the upper edge margins of the respective left and right side walls 117C, 117D. The pouring lips 119 define the left and right sides of the mouth 118. It is understood that during operation, the pharmaceuticals P will only move or flow over one of the pouring lips 119.

Figure 9:
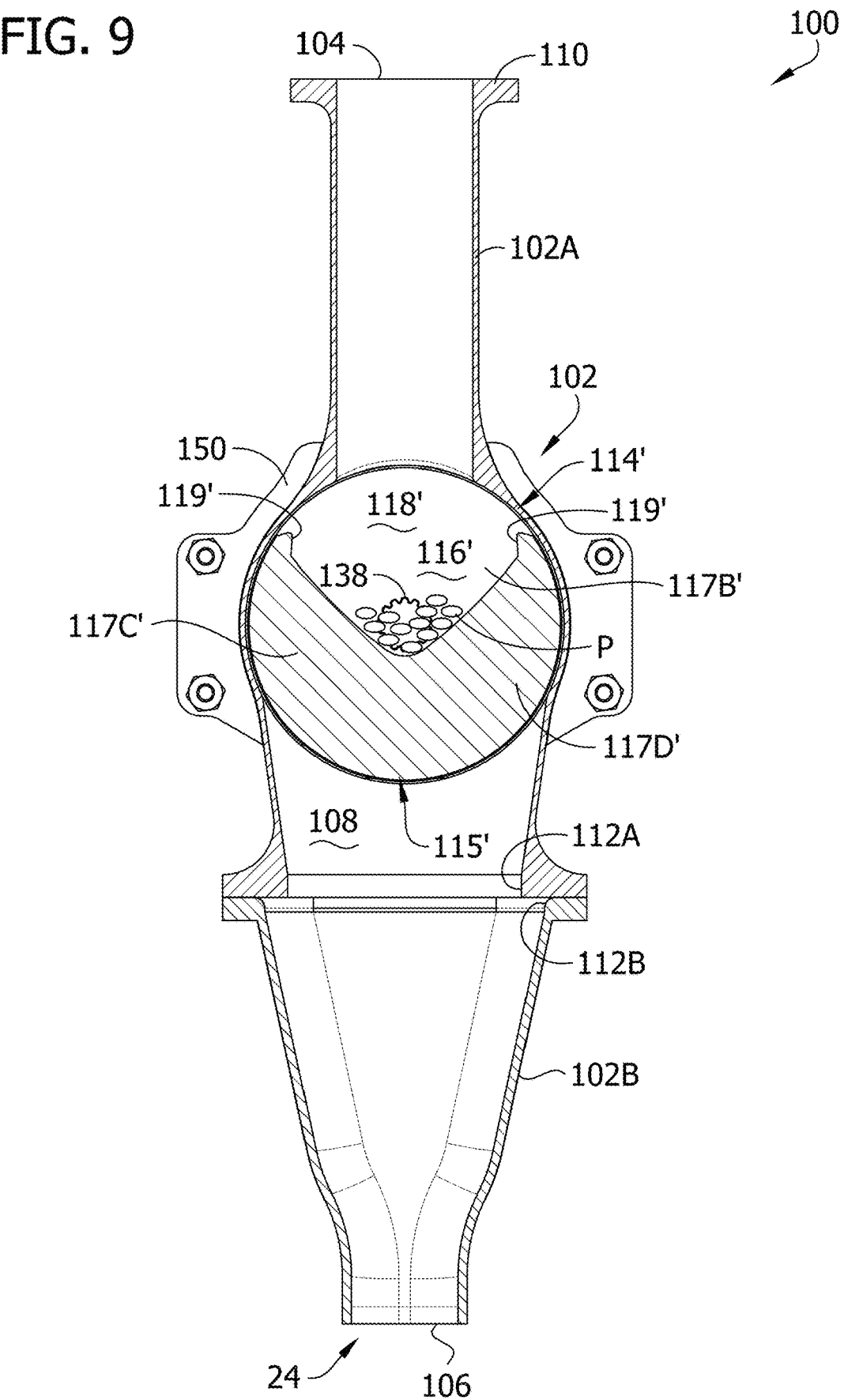
FIG. 9 is a cross section, similar to FIG. 4, of another embodiment of a pharmaceutical gate according to the present disclosure, the pharmaceutical gate including another embodiment of a receiver.

In the illustrated embodiment, the receiver 114 comprises a cup (e.g., has a generally cup shape). The rear side wall 117B has a generally circular or disk shape and the receiver 114 include a generally cylindrical wall 122 (e.g., has a partial cylindrical shape) extending forward from the rear side wall. The cylindrical wall 122 defines (e.g., includes) the base 115 and the left and right side walls 117C, 117D. The cylindrical wall 122 has a cylinder axis CA (FIG. 5) generally aligned with the center of the rear side wall 117B. The receiver 114 is configured to be in close conformance to the housing 102 to inhibit the pharmaceuticals from passing between the housing and the receiver. Specifically, the side walls 117A-D are in close conformance to the housing 102. The cylindrical wall 122 is configured to be in close conformance to the housing 102 to inhibit the pharmaceuticals P from passing between the housing and receiver 114. In an example embodiment, close conformance can be less than one-third of the smallest dimension of a pharmaceutical P that can be dispensed in the system. In an example embodiment, close conformance can be a clearance of less than two millimeters between the housing and the receiver. In an example embodiment, close conformance can be assisted by a bushing intermediate the housing and the receiver to essential have no clearance between the housing and the receiver. The one or more interior surface of the housing 102, defining the pharmaceutical passageway 108, have generally cylindrical shapes to correspond to the cylindrical shape of the side wall 122. The rear side wall 117B and cylindrical wall 122 generally define (e.g., bound) the mouth 118 and the pharmaceutical receiving space 116 (broadly, at least portions thereof). Specifically, the mouth 118 is defined by opposing sides or edge (e.g., pouring lips 119) of the cylindrical wall 122. In one embodiment, the edges (e.g., pouring lips 119) of the cylindrical wall 122 may be rounded or filleted to facilitate the flow of the pharmaceuticals P from the pharmaceutical receiving space 116. The free end of the side wall 122 (e.g., the end opposite the rear side wall 117B) is configured to be in close conformance with the housing 102 when the receiver 114 is disposed in the pharmaceutical passage 108. In this manner, the housing 102 (e.g., a portion or wall thereof) generally defines one end (e.g., the front side wall 117A) of the pharmaceutical receiving space 116 and the mouth 118, with the opposite end of the pharmaceutical receiving space and the mouth defined by the rear side wall 117B. In the illustrated embodiment, the cylindrical wall 122 includes a generally circumferential lip 124 (FIG. 5) at the free end sized and shaped to extend into a circumferential groove or recess 126 in the housing 102. This overlapping of the receiver 114 and housing 102 facilities the positioning of the receiver in the pharmaceutical passage 108 and further inhibits the pharmaceuticals P from passing between the housing and receiver. Accordingly, the portion of the housing 102 defining the section (e.g., intermediate section or portion) of the pharmaceutical passage 108 the receiver 114 is disposed in and generally corresponds to the size and shape of the receiver and closely conforms to the receiver to form a generally tight fight. This generally tight fit between the housing 102 and the receiver 114 prevents any pharmaceuticals P from passing therebetween and inadvertently flowing out of the pharmaceutical gate 100. For example, the clearance between the housing 102 and the receiver 114 is less than the size of the smallest pharmaceutical P dispensed by the pharmaceutical gate 100. Other configurations of the receiver are within the scope of the present disclosure. For example, in one embodiment, the front side wall 117A is a separate component from the housing 102 and is fixed to and rotates with (e.g., is apart of) the receiver 114. Furthermore, in one embodiment, the receiver may include a shallower pharmaceutical receiving space. For example, referring to FIG. 9, a receiver 114' with a shallower pharmaceutical receiving space 116' is shown. In this embodiment, components of receiver 114' similar or analogous to components of receiver 114 are designated by the same reference number with a trailing prime. The shallower pharmaceutical receiving space 116' may be fore suitable for smaller pharmaceuticals P. In addition, in this embodiment, the receiver 114' includes lips 119', defining the mouth 118', that extend generally toward one another. The lips 119 help retain the pharmaceutical P in the pharmaceutical receiving space 116' until the receiver is positioned to dispense the pharmaceuticals.

Figure 10:
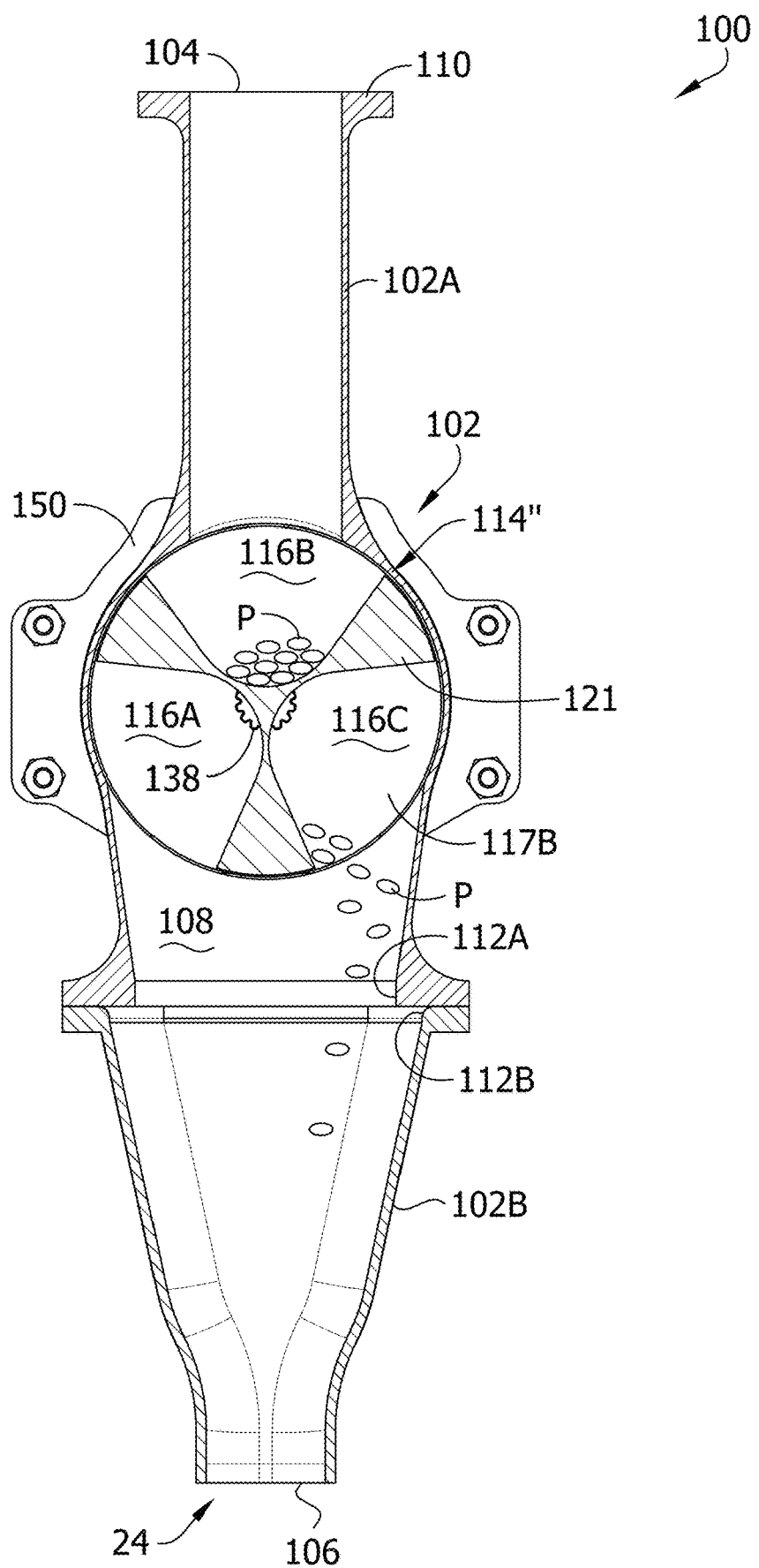
FIG. 10 is a cross section, similar to FIG. 4, of another embodiment of a pharmaceutical gate according to the present disclosure, the pharmaceutical gate including another embodiment of a receiver.

Moreover, in one embodiment, the receiver may include two or more pharmaceutical receiving spaces in order to stage or buffer multiple groups of prescriptions (e.g., multiple prescriptions orders of pharmaceuticals P) from the pharmaceutical counter 12. This may allow the pharmaceutical dispenser 10 to dispense pharmaceuticals P at a faster rate. For example, referring to FIG. 10, a receiver 114" with three pharmaceutical receiving spaces 116A-C is shown. The receiver 114" operates in generally the same manner as receiver 114, as described herein, except the receiver 114" only rotates about 120 degrees at a time to dispense the pharmaceuticals P. In this embodiment, instead of side wall 122, the receiver 114" includes an interior body 121 having three legs extending outward from a center (aligned with the axis of rotation) of the body. The legs are generally equally spaced apart and define the sides and mouth of each receiving space 116A-C.

Figure 4A:
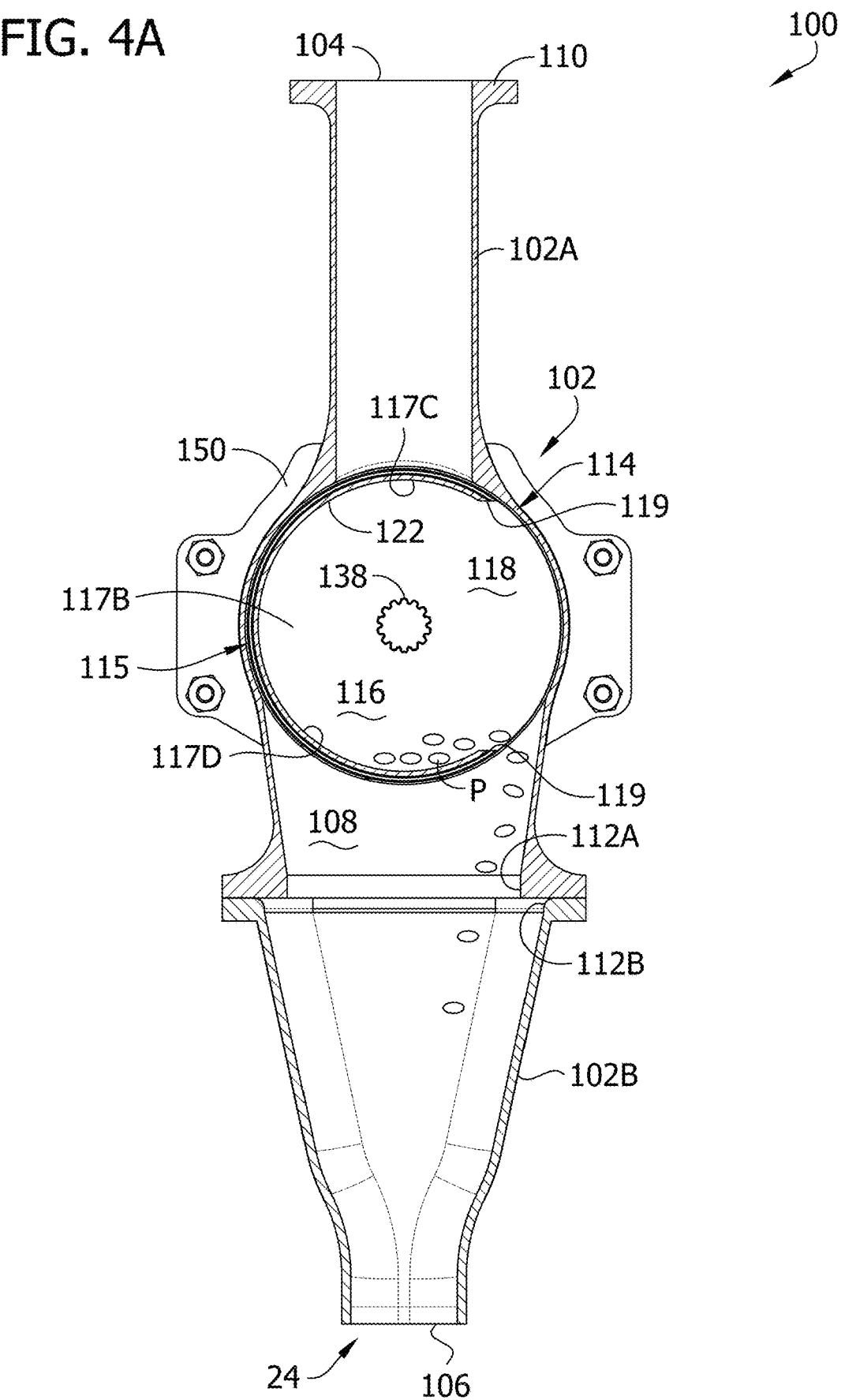
FIG. 4A is a cross section of the pharmaceutical gate taken through line 4-4 of FIG. 3 with the receiver in a pouring position.

Referring back to FIGS. 4-6, the receiver 114 is movable between a receiving position, as shown in FIGS. 4 and 5, a pouring position, as shown in FIG. 4A, and a dispensing position, as shown in FIG. 6. Specifically, the receiver 114 turns between the receiving position, the pouring position and the dispensing position. In the illustrated embodiment, the receiver 114 turns (e.g., rotates) approximately 180 degrees between the receiving position and the dispensing position (e.g., the receiver generally flips over). The receiver 114 rotates between the receiving and dispensing positions about a rotational axis RA (FIG. 5). The rotational axis RA may be spaced apart from the receiver 114 or extend through the receiver. In the illustrated embodiment, the rotational axis RA and cylinder axis CA are generally coextensive. In the receiving position, the receiver 114 is configured to receive the pharmaceuticals P from the pharmaceutical counter 12. The receiver 114 receives the pharmaceuticals P in the pharmaceutical receiving space 116 as the pharmaceuticals flow through the inlet opening 104. In the receiving position, the mouth 118 faces the inlet opening 104. In the illustrated embodiment, the mouth 118 faces generally upward to receive the pharmaceuticals P flowing generally downward in the pharmaceutical passage 108. The pharmaceuticals P flow (e.g., fall) into the pharmaceutical receiving space 116 and are held (e.g., stored, staged) there until the receiver moves toward the dispensing position. Thus, the receiver 114 blocks the pharmaceuticals P from reaching the outlet opening 106 when in the receiving position.

The pouring position (FIG. 4A) is intermediate the receiving position and the dispensing position. In the pouring position, the receiver 114 is positioned to permit at least some of the pharmaceuticals P to move (e.g., flow, pour) out of the pharmaceutical receiving space 116. In the pouring position, the one of the pouring lips 119 is spaced apart from a wall (e.g., side wall) of the housing 102, thereby permitting the pharmaceuticals P to flow out of the receiver 114 through the mouth 118. The pouring position may be generally any position between the receiving and dispensing positions where the pharmaceuticals P can flow out of the receiver 114 (e.g., where the mouth 118 is not covered or blocked by the housing 102). In this position, the pharmaceuticals pour from the receiver 114 over one of pouring lips 119 (e.g., the right pouring lip in the illustrated embodiment). The pharmaceuticals P are poured into the lower portion of the pharmaceutical passage 108. In the pouring position, one of the pouring lips 119 (e.g., the right pouring lip) is located or disposed higher than the lower most point or portion of the pharmaceutical receiving space 108. As explained in more detail below, this configuration facilitates the gradual pouring of the pharmaceuticals P from the receiver 114.

In the dispensing position (FIG. 6), the receiver 114 is configured to dispense (e.g., permit the pharmaceuticals P flow out of the pharmaceutical receiving space 116) the pharmaceuticals through the outlet opening 106 (e.g., toward the pharmaceutical outlet 24 and container station 20). The receiver 114 permits the pharmaceuticals P to flow out of the pharmaceutical receiving space 116 toward the container C positioned at the container station 20. It is understood that at least a portion (e.g., all) of the pharmaceuticals P may fall out of the pharmaceutical receiving space 116 before the receiver 114 is moved fully to the dispensing position—i.e., the pouring position. In other words, at least some of the pharmaceuticals P will flow out of the receiver 114 as the receiver moves toward the dispensing position. In the dispensing position, no portion of the pharmaceutical receiving space 116 is disposed below the pouring lip 119. This ensures all of the pharmaceuticals P have been dispensed. Once the receiver 114 is in the dispensing position, all of the pharmaceuticals P will flow out (or will have flown out) of the pharmaceutical receiving space 116. The pharmaceuticals P flow from the container receiving space 116 into a lower portion of the pharmaceutical passage 108 extending to the outlet opening 106. This lower portion of the pharmaceutical passage 108 is tapered to conform the size and shape of the pharmaceutical passage 108 and the outlet opening 106 to the size and shape of either the opening of the container C, as shown in FIG. 1, or to the size and shape of any pharmaceutical plumbing (not shown) extending from the outlet opening, in other embodiments. In the illustrated embodiment, the lower portion of the pharmaceutical passage 108 tapers inward. The taper is gradual to prevent the pharmaceuticals P from becoming stuck or trapped in the pharmaceutical passage 108. In the dispensing position, the mouth 118 faces the outlet opening 106. In the illustrated embodiment, the mouth 118 faces generally downward to permit the pharmaceuticals P to flow generally downward in the pharmaceutical passage 108, toward the pharmaceutical outlet 24.

The receiver 114 is configured to dispense the pharmaceuticals P in a controlled pour. In an exemplary embodiment, the receiver 114 rotates at about 5-15 rpm such that the pharmaceuticals P pour over the edge or lip 119 in a more singulated manner than a faster rotation which would cause a plurality of or all of the pharmaceuticals P to pour out of the receiver at the same time. The number of pharmaceuticals P in the receiver can be 30×N (30 times N), with N being an integer (e.g., the number of months in a prescription for the pharmaceuticals P). In an example, the pharmaceuticals P pour out of the receiver 114 over a length of time about 1 or 1.5 seconds or greater, e.g., about 2 seconds, about 3 seconds (+/−0.5 seconds).

The pharmaceutical gate 100 includes a prime mover 130 operatively coupled to the receiver 114 to move (e.g., rotate) the receiver between the receiving position and the dispensing position. The prime mover 130 may be an electric motor, a stepper motor, a servo motor, a solenoid, or any other suitable device. In the illustrated embodiment, the pharmaceutical gate 100 includes a transmission 132 operatively coupling the prime mover 130 to the receiver 114. The transmission 132 includes a drive shaft 134 with a drive gear 136 at the end thereof to drive movement (e.g., rotation) of the receiver 114. The transmission 132 may include one or more internal gears (not shown) that are driven by the prime mover 130 and, in turn, drive movement of the drive shaft 134. The drive gear 136 meshes with teeth 138 on the receiver 114 to move the receiver. In the illustrated embodiment, drive shaft 134, the drive gear 136 and the teeth 138 are all generally aligned with the central axis CA. Other configurations are within the scope of the present disclosure.

Referring to FIGS. 2-7, the pharmaceutical gate 100 includes a mounting bracket 152 for mounting the prime mover 130, the transmission 132 and the receiver 114 to the housing 102. The prime mover 130 and transmission 132 are secured to the mounting bracket 152 with fasteners 154 (e.g., bolts), which extend though aligned openings in the transmission and mounting bracket. In the illustrated embodiment, the teeth 138 of the receiver 114 generally form a friction fit with the driver gear 136, thereby mounting the receiver to the mounting bracket 152 (via the transmission). The housing 102 includes a motor mounting flange 150 used to mount the mounting bracket 152 (e.g., prime mover 130, transmission 132, and receiver 114) to the housing. The mounting bracket 152 is secured to the housing 102 with fasteners 156 (e.g., bolts) that extend through aligned openings in the mounting bracket and motor mounting flange 150. Such a configuration allows the pharmaceutical gate 100 to be easily disassembled for periodic maintenance and/or cleaning.

Figure 8:
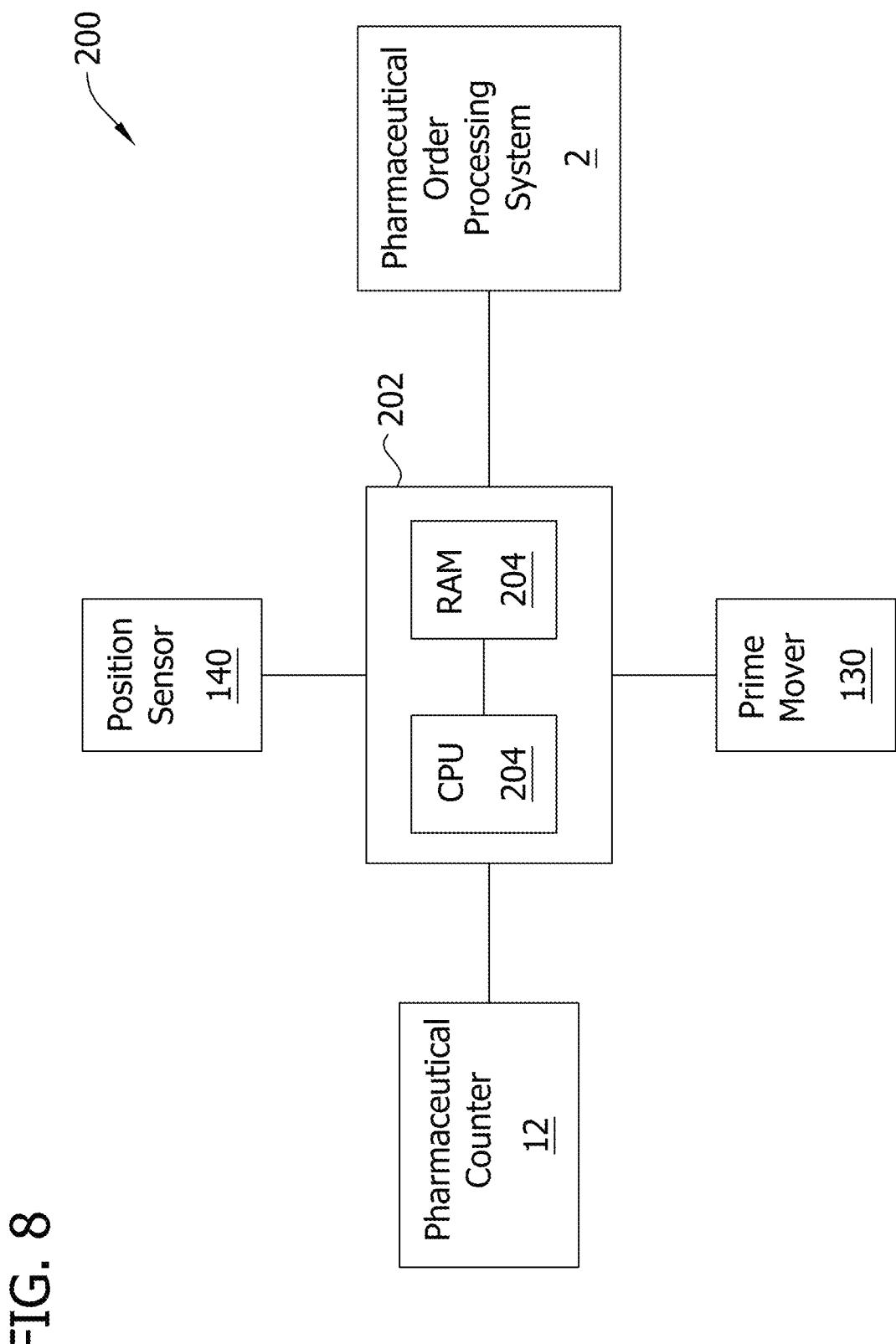
FIG. 8 is a diagram of an exemplary control system of the pharmaceutical dispenser.

Referring to FIG. 8, an exemplary control system (e.g., a gate control system) for the pharmaceutical dispenser 10 (e.g., pharmaceutical gate 100) is generally indicated by reference numeral 200. The control system 200 includes a controller 202 (broadly, a computer) for controlling the operation of the pharmaceutical gate 100. In the illustrated embodiment, the controller 202 (e.g., a gate controller) is a dedicated controller for the pharmaceutical dispenser 10 and is in communication with the pharmaceutical order processing system 2. In other embodiments, the controller 202 may be an existing controller of the pharmaceutical order processing system 2. The controller 202 can control one or more pharmaceutical gates 100. The controller 202 includes a CPU or processor 204 (e.g., a gate processor) and RAM or memory 206 (broadly, non-transitory computer-readable storage medium). The controller 202 controls and operates the various components (e.g., prime mover 130, counter 12 etc.) of the pharmaceutical dispenser 10. Broadly, the memory 206 includes (e.g., stores) processor-executable instructions for controlling the operation of the pharmaceutical dispenser 10 and the components thereof. The instructions embody one or more of the functional aspects of the pharmaceutical dispenser 10 and the components thereof, with the processor 204 executing the instructions to perform said one or more functional aspects. The components of the pharmaceutical dispenser 10 (e.g., pharmaceutical gate 100) may be in wired or wireless communication with the controller 202. Other configurations of the control system 200 are within the scope of the present disclosure.

The controller 202 is communicatively coupled to the pharmaceutical counter 12. The controller 202 is configured to operate the pharmaceutical counter 12. The controller 202 can instruct (e.g., tell) the pharmaceutical counter 12 when to release the pharmaceuticals P and the number or quantity of pharmaceuticals to release. The controller 202 receives this information from the pharmaceutical order processing system 2 (e.g., from the prescription order). Desirably, the controller 202 only operates the pharmaceutical counter 12 to release the pharmaceuticals P when the receiver 114 is in the receiving position. The controller 202 is also communicatively coupled to the prime mover 130 and is configured to operate the prime mover to move the receiver 114 to and between the receiving and dispensing positions. To receive the pharmaceuticals P, the controller 202 operates the prime mover 130 to move the receiver 114 to the receiving position. To dispense the pharmaceuticals P, the controller 202 operates the prime mover 130 to move the receiver 114 toward (e.g., to) the dispensing position. Desirably, the controller 202 only operates the prime mover 130 to move the receiver 114 toward the dispensing position when (e.g., after) a container C is in a position to receive the pharmaceuticals P at the container station 20. The controller 202 may receive information from the pharmaceutical order processing system 2 about when a container C is positioned at the container station 20. For example, the controller 202 may receive a signal from the pharmaceutical order processing system 2 indicating a container C is at the container station 20 and thereby operate the prime mover 130 to move the receiver 130, in response to the signal, toward the dispensing position to dispense the pharmaceuticals P into the container.

In one embodiment, the controller 202 is configured to know what position the receiver 114 is in (e.g., the receiving position, the dispensing position, or somewhere in-between). For example, in some embodiments, the prime mover 130 (e.g., a stepper motor) may know its position, which can be relayed to the controller 202. The controller 202 may then be able to correlate the prime mover's 130 position to the position of the receiver 114 relative to the receiving and dispensing positions. In other embodiments, the pharmaceutical gate 100 may include one or more position sensors 140 to sense the position of the receiver 114. The position sensors 140 are in communication with the controller 202 and can send a signal to the controller when the receiver 114 is in the receiving or dispensing positions (broadly, at least one of the receiving or dispensing positions). For example, the pharmaceutical gate 100 may include one position sensor 140 to tell the controller 202 when the receiver 114 is in the receiving position and another position sensor to tell the controller when the receiver is in the dispensing position. The controller 202 can use this information from the prime mover 130 or position sensor 140 to confirm the position of the receiver 114 before taking an action. For example, the controller 202 can use this information to confirm (e.g., determine) that the receiver 114 is in the receiving position, and thereby ready to receive the pharmaceuticals P, before instructing the pharmaceutical counter 12 to release the pharmaceuticals. Moreover, if the controller 202 determines the receiver 114 is not the in the receiving position, it can control the pharmaceutical counter 12 to prevent the counter from releasing any pharmaceuticals P until the controller determines the receiver is in the receiving position. Likewise, the controller 202 can use this information to confirm that the receiver 114 is in the dispensing position, and has thereby dispensed the pharmaceuticals P. The controller 202 may relay this information to the pharmaceutical order processing system 2, which can then remove the now filled container C from the container station 20.

The pharmaceutical gate 100 is configured to dispense the pharmaceuticals P in a controlled pour toward the pharmaceutical outlet 24. In contrast to dumping or releasing all the pharmaceuticals P at generally the same time (e.g., simultaneously), a controlled pour gradually and steadily pours the pharmaceuticals P out of the receiver 114. For example, the controlled pour may generally dispense the pharmaceuticals P in a generally singulate manner. For example, the controlled pour may generally dispense the pharmaceuticals one after another (e.g., individually). In another example, the controlled pour may generally dispense the pharmaceuticals P (e.g., the pharmaceutical flow over the lip 119) in small groups, such as generally two to ten (or any number therebetween) at a time. By dispensing the pharmaceuticals P in a controlled pour, the likelihood of the pharmaceuticals becoming stuck, blocked or trapped is greatly reduced, especially over prior art mechanisms which generally dispensed all the pharmaceuticals at the same time. The receiver 114 is configured to dispense the pharmaceuticals P in the controlled pour toward the container C at the container station 20. As mentioned above, the interior surfaces of the left and right side walls 117C, 117D defining the pharmaceutical receiving space 116 are arcuate or curved (e.g., concave). Specifically, the pharmaceutical receiving space 116 of the receiver 114 has a generally cylindrical shape (e.g., a generally circular or C-shaped cross section). Other shapes, such as a generally U-shaped cross section, of the pharmaceutical receiving space 116 are within the scope of the present disclosure. As a result, the pharmaceutical receiving space 116 is relatively deep (e.g., the distance from the mouth 118 to the opposite end of the receiving space is relatively large compared to the size of the pharmaceuticals P). Accordingly, the pharmaceuticals P generally collect in the bottom of the pharmaceutical receiving space 116 of the receiver 114 (FIG. 4), spaced apart from the mouth 118. As the receiver 114 is rotated from the receiving position to the dispensing position, the pharmaceuticals P in the receiver gradually move along the arcuate side wall 122 and migrate toward the mouth 118 (e.g., one of the pouring lips 119). This gradual migration toward the mouth 118 as the receiver 114 rotates results in the pharmaceuticals P moving through the mouth and into the pharmaceutical passage 108 (e.g., fall through the passage) in a controlled pour. The arcuate side walls 117C, 117D allow the pharmaceuticals P to generally collect below the pouring lip 119 as the receiver 114 is rotated toward the dispensing position so that the pharmaceuticals generally pour over the pouring lip one at a time instead of all at once. To facilitate this movement, the controller 202 may also be configured to operate the prime mover 130 to control the rotational speed of the receiver 114 as the receiver moves toward the dispensing position in order to dispense the pharmaceuticals in the controlled pour. For example, the controller 202 may operate the prime mover 130 to rotate the receiver 114 between the inclusive range of about 5-15 rpm in order to dispense the pharmaceuticals P in a controlled pour. The controlled pour may take about 1 second, about 1.5 seconds, about 2 seconds, about 3 seconds or greater (broadly, greater than about 1 second) so that the pharmaceuticals P flow in a generally singulate manner. The rotational speed of the receiver 114 may depend on the size of the pharmaceuticals P, the type of pharmaceutical, the brittleness of the pharmaceutical, etc. For example, the receiver 114 can rotate at a faster speed for smaller pharmaceuticals P than compared to the rotational speed for larger pharmaceuticals. In one embodiment, the controller 202 may receive input (e.g., user input), such as by a user interface (not shown) or from the pharmaceutical counter 12, regarding the size of the pharmaceuticals P being dispensed by the pharmaceutical dispenser 10 and control the rotational speed of the receiver 114 accordingly based of this information (e.g., set the speed of rotation to correspond to the size of the pharmaceutical).

In one embodiment, the controller 202 rotates the receiver 114 at the same continuous speed as the receiver moves toward the dispensing position. In another embodiment, the controller 202 rotates the receiver 114 at different speeds as the receiver moves toward the dispensing position. For example, the controller 202 can first rotate the receiver 114 from to the receiving position to an intermediate position at a first speed and then rotate the receiver from the intermediate position to the dispensing position at a second speed. The intermediate position may be the point where the mouth 118 (e.g., a portion thereof) of the receiver 114 is no longer blocked or covered by the housing 102 thereby allowing the pharmaceuticals P to flow through the mouth (e.g., a pouring position), into the lower portion of pharmaceutical passage 108 and toward the pharmaceutical outlet 24. The first speed can be faster than the second speed but too fast to dispense the pharmaceuticals P in a controlled pour, which the second speed is suited for. By varying the speed, the overall cycle time (e.g., the time it takes the receiver to move from the receiving position, to the dispensing position and then back to the receiving position) can be reduced, enabling the pharmaceutical dispenser 10 to dispense more pharmaceuticals P in a given timeframe.

In one exemplary method of operation of the pharmaceutical dispenser 10, the controller 202 receives an indication (e.g., signal) containing the number or quantity of pharmaceuticals P to be dispensed from the pharmaceutical order processing system 2. This indication is based on a pharmaceutical order received by the pharmaceutical order processing system 2. The controller 202 then proceeds to operate the pharmaceutical dispenser 10 to dispense the necessary quantity of pharmaceuticals P need to fulfil the prescription order. The controller 202 may confirm the receiver 114 of the pharmaceutical gate 100 is in the receiving position. The controller 202 then operates the pharmaceutical counter 12 to count the quantity of pharmaceuticals P needed to fulfil the prescription order. The pharmaceutical counter 12 releases the counted pharmaceuticals P which then flow to the pharmaceutical gate 100, via the pharmaceutical plumbing 22. The pharmaceuticals P are counted and released from the hopper 14 which has been pre-filled with the pharmaceuticals by the counting mechanism 16 of the pharmaceutical counter 12. The pharmaceuticals P are then collected by the pharmaceutical gate 100. The pharmaceuticals P flow into the pharmaceutical receiving space 116 of the receiver 114. The pharmaceuticals P remain in (e.g., are stored in) the receiver 114 until they are to be dispensed into a container C.

Before the pharmaceuticals P are dispensed from the pharmaceutical gate 100, the container C is positioned at the container station 20 by the pharmaceutical order processing system 2. The container C is arranged in the container station 20 to receive the pharmaceuticals P from the pharmaceutical outlet 24 when the pharmaceuticals are dispensed by pharmaceutical gate 100. The controller 202 receives a signal from the pharmaceutical order processing system 2 once the container C is positioned at the container station 20. This signal may include directives telling the controller 202 to dispense the pharmaceuticals P or may include information telling the controller container C is now in position at the container station 20, at which point the controller responds by dispensing the pharmaceuticals. The pharmaceuticals P in the pharmaceutical gate 100 are dispensed toward the container C at the container station 20 by moving the receiver 114 toward the dispensing position. The controller 202 operates the prime mover 130 to rotate the receiver 114 to the dispensing position. As the receiver 114 moves toward the dispensing position, the receiver reaches a pouring position and the pharmaceuticals P begin to flow out of the receiver 114. As the receiver 114 continues to move toward the dispensing position (e.g., to and through different pouring positions), the pharmaceuticals P continue to pour over the pouring lip 119 and into the lower portion of the pharmaceutical passage 108. Once the receiver 114 is in the dispensing position, all the pharmaceuticals P have flowed out or will flow out of the pharmaceutical receiving space 116. As mentioned above, desirably, the pharmaceuticals P are dispensed in a controlled pour toward the container C. The controller 202 may control the rotational speed of the receiver 114 as the receiver rotates toward the dispensing position so that the pharmaceuticals P flow out of the receiver in the controlled pour. The pharmaceuticals P then flow through the remainder (e.g., lower portion) of the pharmaceutical passage 108, and if present any additional pharmaceutical plumbing (not shown), through the pharmaceutical outlet 24 and into the container C at the container station 20.

The controller 202 may confirm the pharmaceuticals P have been dispensed by confirming the receiver 114 is in the dispensing position. The controller 202 may then send a signal to the pharmaceutical order processing system 2 indicating the pharmaceuticals P have been dispensed and are in the container C so that the pharmaceutical order processing system can remove the container C from the container station 20. The pharmaceutical order processing system 2 may then further process (e.g., close, package, mail, ship, etc.) the container C in order to deliver the now filled container C to the customer. After the pharmaceuticals P have been dispensed from the pharmaceutical gate 100, the controller 202 may operate the prime mover 130 to rotate the receiver 114 back to the receiving position. The cycle then repeats for the next container C to be filled with the pharmaceuticals P from the pharmaceutical dispenser 10.

While the above description describes the present system as dispensing a plurality of pharmaceuticals P in a controlled manner, it is understood that the systems and methods described herein can be used to dispense other solid, dry items that can be counted (e.g. small objects). For example, the systems and methods described herein can be used to dispense candy, pills, tablets, small toys (e.g., rubber bouncy balls), and the like.

Although described in connection with an exemplary computing system environment, embodiments of the aspects of the disclosure are operational with numerous other general purpose or special purpose computing system environments or configurations. The computing system environment is not intended to suggest any limitation as to the scope of use or functionality of any aspect of the disclosure. Moreover, the computing system environment should not be interpreted as having any dependency or requirement relating to any one or combination of components illustrated in the exemplary operating environment. Examples of well-known computing systems, environments, and/or configurations that may be suitable for use with aspects of the disclosure include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the aspects of the disclosure may be described in the general context of data and/or processor-executable instructions, such as program modules, stored one or more tangible, non-transitory storage media and executed by one or more processors or other devices. Generally, program modules include, but are not limited to, routines, programs, objects, components, and data structures that perform particular tasks or implement particular abstract data types. Aspects of the disclosure may also be practiced in in distributed computing environments where tasks are performed by remote processing devices that are linked through a communications network. In a distributed computing environment, program modules may be located in both local and remote storage media including memory storage devices.

In operation, processors, computers and/or servers may execute the processor-executable instructions (e.g., software, firmware, and/or hardware) such as those illustrated herein to implement aspects of the disclosure.

Embodiments of the aspects of the disclosure may be implemented with processor-executable instructions. The processor-executable instructions may be organized into one or more processor-executable components or modules on a tangible processor readable storage medium. Aspects of the disclosure may be implemented with any number and organization of such components or modules. For example, aspects of the disclosure are not limited to the specific processor-executable instructions or the specific components or modules illustrated in the figures and described herein. Other embodiments of the aspects of the disclosure may include different processor-executable instructions or components having more or less functionality than illustrated and described herein.

The order of execution or performance of the operations in embodiments of the aspects of the disclosure illustrated and described herein is not essential, unless otherwise specified. That is, the operations may be performed in any order, unless otherwise specified, and embodiments of the aspects of the disclosure may include additional or fewer operations than those disclosed herein. For example, it is contemplated that executing or performing a particular operation before, contemporaneously with, or after another operation is within the scope of aspects of the disclosure.

The Title, Field, and Background are provided to help the reader quickly ascertain the nature of the technical disclosure. They are submitted with the understanding that they will not be used to interpret or limit the scope or meaning of the claims. They are provided to introduce a selection of concepts in simplified form that are further described in the Detailed Description. The Title, Field, and Background are not intended to identify key features or essential features of the claimed subject matter, nor is it intended to be used as an aid in determining the claimed subject matter.

When introducing elements of aspects of the disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that several advantages of the aspects of the disclosure are achieved and other advantageous results attained.

Not all of the depicted components illustrated or described may be required. In addition, some implementations and embodiments may include additional components. Variations in the arrangement and type of the components may be made without departing from the spirit or scope of the claims as set forth herein. Additional, different or fewer components may be provided and components may be combined. Alternatively or in addition, a component may be implemented by several components.

The above description illustrates the aspects of the disclosure by way of example and not by way of limitation. This description enables one skilled in the art to make and use the aspects of the disclosure, and describes several embodiments, adaptations, variations, alternatives and uses of the aspects of the disclosure, including what is presently believed to be the best mode of carrying out the aspects of the disclosure. Additionally, it is to be understood that the aspects of the disclosure is not limited in its application to the details of construction and the arrangement of components set forth in the description or illustrated in the drawings. The aspects of the disclosure are capable of other embodiments and of being practiced or carried out in various ways. Also, it will be understood that the phraseology and terminology used herein is for the purpose of description and should not be regarded as limiting.

Having described aspects of the disclosure in detail, it will be apparent that modifications and variations are possible without departing from the scope of aspects of the disclosure as defined in the appended claims. It is contemplated that various changes could be made in the above constructions, products, and methods without departing from the scope of aspects of the disclosure. In the preceding specification, various embodiments have been described with reference to the accompanying drawings. It will, however, be evident that various modifications and changes may be made thereto, and additional embodiments may be implemented, without departing from the broader scope of the aspects of the disclosure as set forth in the claims that follow. The specification and drawings are accordingly to be regarded in an illustrative rather than restrictive sense.

What is claimed is:

1. A dispenser gate for dispensing a specified quantity of a plurality of items into a container, the pharmaceutical dispenser comprising:
    a housing; and
    a receiver positioned in the housing, the receiver being sized and shaped to define a receiving space to receive the quantity of items, hold the quantity of items and pour the quantity of items, the receiver being movable from a receiving position toward a pouring position at a speed which varies as the receiver moves from the receiving position toward the pouring position, at the receiving position the receiver is arranged to receive the quantity of items in the receiving space from a counter, and in the pouring position the receiver is arranged to begin pouring the quantity of items in a controlled pour over a pouring lip toward an outlet, the pouring lip extending into the opening of the receiving space.

2. The dispenser gate according to claim 1, wherein the receiver includes a fixture operatively connected to a prime mover configured to move the receiver in a first direction, the first direction being generally toward the pouring position from the receiving position, the prime mover configured to vary the speed the receiver moves at as the receiver moves in the first direction.

3. The dispenser gate according to claim 1, wherein the housing includes a recess, and wherein the receiver includes a wall at least partially defining the receiving space, the wall includes a circumferential lip extending into the recess in the housing.

4. The dispenser gate according to claim 1, wherein the pouring lip retards some items from immediately flowing from the receiving space out to a container.

5. The dispenser gate of claim 1, wherein the housing defines an exit passage to receive the items from the receiver at the pouring position, and wherein the exit passage is filleted to reduce likelihood of items being trapped from passage to the container.

6. The dispenser gate of claim 1, wherein the housing defines an exit passage to receive the items from the receiver at the pouring position, the exit passage includes a mouth to receive the items from the receiver, the mouth of the exit passage is wider than the opening of the receiving space.

7. The dispenser gate of claim 6, wherein the housing defines an entry passage to pass the quantity of items to the receiver, wherein the entry passage includes a mouth at the receiver that is wider than an opening of the receiving space.

8. The dispenser gate of claim 1, wherein the housing defines an entry passage to pass the quantity of items to the receiver, wherein the entry passage includes a mouth at the receiver that is wider than an opening of the receiving space.

9. The dispenser gate of claim 1, wherein the receiver includes arcuate walls defining the receiving space.

10. The dispenser gate of claim 1, wherein the receiver includes non-planar walls defining the receiving space.

11. A dispenser gate for dispensing a specified quantity of a plurality of items into a container, the pharmaceutical dispenser comprising:
    a housing including an interior wall, an entry passage and an exit passage; and
    a receiver positioned in the housing, the receiver being sized and shaped to define a receiving space to receive the quantity of items, hold the quantity of items within the housing, and pour the quantity of items, the receiver being in close conformance with the interior wall of the housing, the receiver being movable in a first direction from a receiving position, past a hold position toward a pouring position at a speed which varies as the receiver moves in the first direction, at the receiving position the receiver is arranged to receive the quantity of items in the receiving space through the entry passage, and in the pouring position the receiver is arranged to begin pouring the quantity of items in a controlled pour over a pouring lip into the exit passage, the pouring lip extending into the opening of the receiving space, wherein the receiver being in close conformance to the interior wall of the housing holds the pills in the receiving space in the hold position between the receiving position and the pouring position.

12. The dispenser gate according to claim 11, wherein the receiver includes a fixture operatively connected to a prime mover configured to move the receiver in the first direction, the prime mover configured to vary the speed the receiver moves at as the receiver moves in the first direction.

13. The dispenser gate according to claim 11, wherein the housing includes a recess adjacent the receiver, and wherein the receiver includes a wall at least partially defining the receiving space, the wall includes a circumferential lip extending into the recess in the housing to fix the receiver in close conformance with the housing.

14. The dispenser gate according to claim 11, wherein the pouring lip retards some items from immediately flowing from the receiving space out to a container.

15. The dispenser gate according to claim 11, wherein the exit passage receives items from the receiving space at the pouring position and is filleted to reduce likelihood of items being trapped from passage to the container.

16. The dispenser gate according to claim 11, wherein the exit passage of the housing includes a mouth to receive the items from the receiver, the mouth of the exit passage is wider than the opening of the receiving space.

17. The dispenser gate according to claim 11, wherein the entry passage of the housing includes a mouth adjacent the receiver that is wider than an opening of the receiving space.

18. The dispenser gate of claim 11, wherein the receiver includes non-planar walls, arcuate walls or a combination thereof defining the receiving space.

19. The dispensing gate of claim 11, wherein the close conformance of the housing and the receiver is less than a dimension of the item such that an item cannot pass between the housing and the receiver.

20. The dispensing gate according to claim 11, wherein the receiver rotates at a first speed in the first direction as the receiver turns toward the pouring position and at a second speed in the first direction after the receiver reaches the pouring position, the second speed being slower than the first speed.

\* \* \* \* \*